United States Patent [19]

Fiedler et al.

[11] Patent Number: 4,988,829
[45] Date of Patent: Jan. 29, 1991

[54] PROCESS FOR THE PREPARATION OF 2-(4-CHLOROPHENYLETHYL)-2-TERT.-BUTYL-OXIRANE

[75] Inventors: Paul Fiedler; Martin Littmann, both of Cologne, Fed. Rep. of Germany; Manfred Lenthe, Overland Park, Kans.; Achim Noak; Gerd Siekmann, both of Cologne, Fed. Rep. of Germany

[73] Assignee: Bayer Aktiengessellschaft, Leverkusen, Fed. Rep. of Germany

[21] Appl. No.: 373,770

[22] Filed: Jun. 30, 1989

[30] Foreign Application Priority Data

Jul. 19, 1988 [DE] Fed. Rep. of Germany ....... 3824457

[51] Int. Cl.$^5$ ............................................ C07D 301/02
[52] U.S. Cl. ..................................... 549/519; 549/563
[58] Field of Search ............................... 549/519, 563

[56] References Cited

U.S. PATENT DOCUMENTS 4,162,258  7/1979  Higo et al. ........................... 549/332

FOREIGN PATENT DOCUMENTS 3315510  10/1984  Fed. Rep. of Germany ...... 549/519

OTHER PUBLICATIONS

V. Frazen et al., Chem. Ber., "Reaction of Sulter Ylides with Polar Double Bonds", 96(7), pp. 1881–1890 (1963), English Abstract of German Patent 3,315,510 (Derwent).

Primary Examiner—Richard L. Raymond
Assistant Examiner—Mark W. Russell
Attorney, Agent, or Firm—Sprung Horn Kramer & Woods

[57] ABSTRACT

A process for making the known fungicide intermediate 2-(4-chlorophenyl ethyl)-2-tert.-butyloxirane of the formula

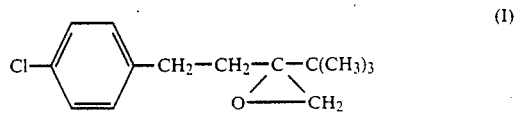

comprising
(a) mixing a solution of trimethylsulphonium bromide of the formula $(CH_3)_3S^{\oplus}Br^{\ominus}$  (II)

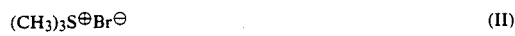

in a methanol/toluene mixture with preheated toluene and simultaneously distilling off a methanol/toluene mixture at a temperature between 65° and 110° C. until a suspension having a solids content between 10 and 70% by weight is formed, and
(b) reacting the suspension of trimethylsulphonium bromide in toluene thus obtained with 1-(4-chlorophenyl)-4,4-dimethylpentan-3-one of the formula

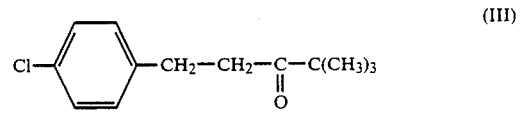

in the presence of solid potassium hydroxide, diethylene glycol and water at a temperature between 20° and 120° C., the amounts of the reaction components being such that per mole of 1-(4-chlorophenyl)-4,4-dimethylpentan-3-one of the formula (III) there are present
between 1 and 2 moles of trimethylsulphonium bromide of the formula (II),
between 2 and 3 moles of solid potassium hydroxide and also
between 0.1 and 10% by weight of diethylene glycol and between 0.5 and 12% by weight of water, relative to 1-(4-chlorophenyl)-4,4-dimethylpentan-3-one of the formula (III).

7 Claims, No Drawings

PROCESS FOR THE PREPARATION OF 2-(4-CHLOROPHENYLETHYL)-2-TERT.-BUTYL-OXIRANE

The present invention relates to a novel process for the preparation of the known 2-(4-chlorophenylethyl)-2-tert.-butyloxirane, which can be used as intermediate for the synthesis of the fungicide 1-(4-chlorophenyl)-3-(1,2,4-triazol-1-ylmethyl)-4,4-dimethylpentan-3-ol.

It has already been disclosed that oxiranes can be prepared by reacting dimethyl sulphide with methyl bromide and then reacting the resulting trimethylsulphonium bromide with carbonyl compounds in the presence of an inert organic solvent and in the presence of a strong base, such as sodium hydride, sodium amide or potassium tert.-butylate (cf. Ber. 96, 1881–1890 (1963)).

Furthermore it is known that 2-(4-chlorophenylethyl)-2-tert.-butyloxirane can be synthesized by treating dimethyl sulphide with methyl bromide in the presence of an inert organic diluent and reacting the resulting trimethylsulphonium bromide with 1-(4-chlorophenyl)-4,4-dimethylpentan-3-one in the presence of a base and also in the presence of an inert organic diluent at temperatures between 0° C. and 60° C. (cf. DE-OS (German Published Specification) No. 3,315,510). It is true that relatively pure 2-(4-chlorophenylethyl)-2-tert.-butyloxirane can be prepared by this process; however, it is a disadvantage that the reaction requires relatively long reaction times and the yield is not always sufficient for practical purposes. It is also unfavorable that the preparation of trimethylsulphonium bromide can only be achieved at a relatively low yield of about 75%. The space/time yields in this process only reach values of about 6 g/l h.

It has now been found that the known 2-(4-chlorophenyl)-2-tert.-butyloxirane of the formula

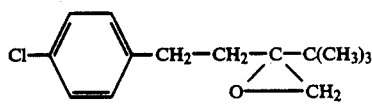

is obtained when (a) a solution of trimethylsulphonium bromide of the formula

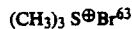   (II)

in a methanol/toluene mixture is introduced into preheated toluene and simultaneously a methanol/toluene mixture is distilled off at temperatures between 65° C. and 110° C. until a suspension having a solids content between 10 and 70% by weight is formed and (b) the suspension of trimethylsulphonium bromide in toluene thus obtained is reacted with 1-(4-chlorophenyl)-4,4-dimethylpentan-3-one of the formula

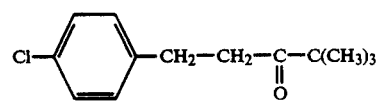   (III)

in the presence of solid potassium hydroxde, diethylene glycol and water at temperatures between 20° C. and 120° C., the amounts of the reaction components being such that 1 mole of 1-(4-chlorophenyl)-4,4-dimethylpentan -3-one of the formula (III)

between 1 and 2 moles of trimethylsulphonium bromide of the formula (II), between 2 and 3 moles of solid potassium hydroxide and also between 0.1 and 10% by weight of diethylene glycol and between 0.5 and 12% by weight of water, relative to 1-(4-chlorophenyl)-4,4-dimethylpentan-3-one of the formula (III), are present.

It is extremely surprising that it is possible to prepare 2-(4-chlorophenylethyl)-2-tert.-butyloxirane of the formula (I) by the process according to the invention in a short period of time and in a significantly higher yield than by the known process in which trimethylsulphonium bromide serves as generator of methylene. The previously known prior art had to lead to the assumption that the reaction according to the invention, in which a reaction between solid trimethylsulphonium bromide and solid potassium hydroxide takes place, would proceed more unfavorably than the previously known reaction in which one reaction is dissolved homogeneously. However, contrary to the expectations, the reaction according to the invention in a heterogeneous medium gives significantly better results than the previously known reaction in which at least one reaction is present in a liquid phase.

The process according to the invention is distinguished by a series of advantages. Thus, the required reaction components are available even on an industrial scale and easy to handle. Since the reaction proceeds very quickly under the conditions according to the invention, space/time yields of 50 to 60 g/h are obtained, which represents a very signficant improvement compared to the previously known process. Another advantage is that the workup of the resulting reaction mixture does not present any difficulties and the 2-(4-chlorophenylethyl)-2-tert.-butyloxirane is obtained in extremely high yield and excellent purity.

The course of the process according to the invention can be illustrated by the following formula scheme:

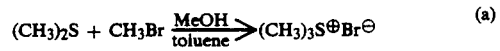   (a)

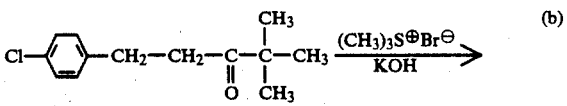   (b)

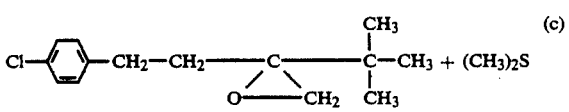   (c)

The 1-(4-chlorophenyl) -4,4-dimethylpentan-3-one of the formula (III), which is required as starting material in the process according to the invention, is known (cf. DE-OS (German Published Specification) No. 3,315,681).

The trimethylsulphonium bromide of the formula (II), which is further required as starting material in the process according to the invention, is also known (cf. Ber. 96, 1881–1890 (1963). It is employed in the reaction according to the invention in the form of a suspension in toluene. This suspension is preferably prepared by reacting methyl bromide and dimethyl sulphide in a boiling toluene/methanol mixture, which contains between 1 and 2.5, preferably between 1.1 and 2.0, parts by weight of methanol per part by weight of toluene. The solution thus obtained is passed into toluene which has been preheated to temperatures between 70° and 110° C. At flask temperatures between 65° C. and 110° C., preferably between 80° C. and 90° C., a methanol/toluene mixture is simultaneously distilled off. It is also possible to carry out the distillation under reduced pressure and low temperature. The amounts of methyl bromide and dimethyl sulphide and toluene and methanol employed are selected such that the suspension formed after the removal of the methanol/toluene mixture by distillation has a solids content between 10 and 70% by weight, preferably between 40 and 50% by weight.

When carrying out the process according to the invention, potassium hydroxide serves as base. It can be used in the form of pellets, flakes, granules or as powder.

The amounts of water and diethylene glycol which are added to the reaction mixture, when the process according to the invention is carried out, can be varied within a certain range. In general, between 0.1 and 10% by weight of diethylene glycol and 0.5 to 12% by weight of water, preferably between 1 and 4% by weight of diethylene glycol and 2 to 8% by weight of water, are used per part by weight of 1-(4-chlorophenyl)-4,4-dimethylpentan-3-one.

When step (b) of the process according to the invention is carried out, the reaction temperatures can be varied within a fairly large range. In general, it is carried out at temperatures between 20° C. and 120° C., preferably between 60° C. and 90° C.

The process according to the invention can be carried out either under inert gas atmosphere or in the absence of any special inert gas atmosphere.

The process according to the invention is in general carried out such that in each case the suspension of trimethylsulphonium bromide in toluene is initially introduced, the required amounts of potassium hydroxide, diethylene glycol and water are added, the mixture is heated to the desired reaction temperature and then the 1-(4-chlorophenyl)-4,4-dimethylpentan-3-one of the formula (III) is added. However, it is also possible to introduce the 1-(4-chlorophenyl)-4,4-dimethylpentan-3-one of the formula (III), potassium hydroxide, diethylene glycol and water initially, then to heat the mixture to the reaction temperature and add the suspension of trimethylsulphonium bromide in toluene. Depending on the particular reaction temperature, the dimethyl sulphide formed in the reaction can either remain in the reaction mixture or be removed by distillation during the reaction.

The workup is in general carried out such that water is added to the reaction mixture, the aqueous phase is separated off, the remaining organic phase is washed with water and then, optionally after previous filtration, concentrated first at atmospheric pressure and then under reduced pressure by distilling off the volatile components.

The 2-(4-chlorophenylethyl)-2-tert.-butyloxirane of the formula (I) preparable by the process according to the invention is a useful intermediate for the synthesis of 1-(4-chlorophenyl)-3-(1,2,4-triazol-1-ylmethyl)-4,4-dimethylpentan-3-ole, which has excellent plant growth regulating and fungicidal properties (cf. EP-OS No. 0,040,345).

The process according to the invention is illustrated by the examples which follow.

PREPARATION EXAMPLES

Example 1

303 g of methyl bromide are passed into a mixture of 365 g of toluene, 679 g of methanol and 235 g of dimethyl sulphide at the boiling temperature over a period of 3 hours. Stirring is continued for one hour. The solution thus obtained is metered into 775 g of toluene at 83°-86° C. over a period of 3 hours. Simultaneously, 1,081 g of a methanol/toluene/dimethyl sulphide mixture (weight ratio 35/65/4) are distilled off through a column with stirring. The suspension thus prepared contains 500 g of trimethylsulphonium bromide yield: 99%, relative to methyl bromide.

467 g of potassium hydroxide granules (88% pure), 34.6 g of water and 11.6 g of diethylene glycol are introduced successively into the stirred suspension at 60° C. 577 g of 1-(4-chlorophenyl)-4,4-dimethylpentan-3-one are subsequently uniformly added over a period of 1.5 hours, and the reaction mixture is heated to 80° C. The mixture is stirred for another 4 hours, cooled to 60° C., poured into 1 kg of water, thoroughly stirred, allowed to settle and the phases are separated.

The organic phase is freed from toluene in vacuo. This gives 601 g of a product consisting, according to the gas chromatogram, of 96.7% by weight of 2-(4-chlorophenylethyl)-2-tert.-butyloxirane. The yield is accordingly calculated to be 94.8% of theory.

Example 2

49 kg of methanol, 26 kg of toluene and 25 kg of dimethyl sulphide are initially introduced into a 250 l stirred kettle made of enamelled steel and heated to reflux. 32 kg of methyl bromide are then introduced over a period of 3 hours. The reaction is allowed to continue for 2 hours at the boiling temperature and this reaction mixture is then introduced via a heated line over a period of 3 hours into a 250 l stirred kettle in which 79 kg of toluene are present at a temperature of 80° C. to 83° C. Simultaneously a mixture of 49 kg of methanol, 26 kg of toluene and 4 kg of dimethyl sulphide are distilled off from this kettle at a flask temperature of 80°-83° C. through a column. The suspension thus prepared contains 53 kg of trimethylsulphonium bromide; the solids content of the suspension is 40% by weight. 47.5 kg of potassium hydroxide granules (88% pure), 2.0 kg of water and 2.5 kg of diethylene glycol are successively added to this stirred suspension at 60° C. The mixture is then heated to 80° C. and 59.0 kg of 1-(4-chlorophenyl)-4,4-dimethylpentan-3-one (98% pure) are uniformly added over a period of 1.5 hours. The reaction mixture is stirred for another 4 hours. Analysis of a sample by gas chromatography shows a conversion of 99.2%. The reaction mixture is worked up by washing it with water, separating off the toluene by steam distillation and drying. 60.7 kg of a product remain, which according to the gas chromatogram consists of 96.2% of 2-(4-chlorophenylethyl)-2-tert.-butyloxirane. The yield is accordingly calculated to be 95.1% of theory.

Comparative Example 95 g of methyl bromide are introduced into a solution of 62 g of dimethyl sulphide in 300 ml of acetone at 20° C. over a period of 4 hours. Stirring is continued for 10 hours, the precipitated trimethylsulphonium bromide is then filtered off with suction and the salt is dried at 30° C. 115 g (73% of theory) of trimethylsulphonium bromide are obtained in this manner.

22.4 g of 1-(4-chlorophenyl)-4,4-dimethylpentan3-one are added to a mixture of 22.4 g of potassium tert.-butylate in 100 ml of tert.-butanol at room temperature with stirring. 23.5 g of trimethylsulphonium bromide are then added, in the course of which the temperature of the reaction mixture rises to 30° C. After stirring for another 22 hours at room temperature, quantitative conversion is achieved. According to analysis by gas chromatography, the content of the desired final product is 98.8%. The reaction mixture is worked up by adding successively 200 ml of water and 20 ml of aqueous sodium hypochlorite solution.

The mixture is then extracted with a total of 250 ml of ethylene chloride, the organic phase is washed with water until neutral and subsequently concentrated by drawing off the solvent under reduced pressure. An oily residue of 21.1 g remains, which according to the gas chromatogram consists of 95.9% of 2-(4-chlorophenylethyl)2-tert.-butyloxirane. Accordingly a yield of 84.8% of theory is calculated.

The foregoing oxirane of the formula (I) can be converted into the fungicidal compound of the formula

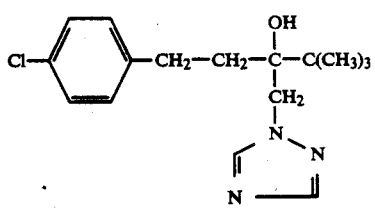

(IV)

as set forth in the U.S. Pat. No. 4,723,984 and in DE-OS No. (German Published Specification) 3,315,510.

It will be understood that the specification and examples are illustrative but not limitative of the present invention and that other embodiments within the spirit and scope of the invention will suggest themselves to those skilled in the art.

We claim:

1. A process for the preparation of 2-(4-chlorophenyl ethyl)-2-tert.-butyloxirane of the formula

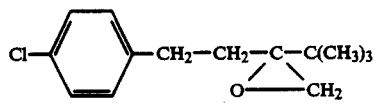

(I)

comprising
(a) mixing a solution of trimethylsulphonium bromide of the formula

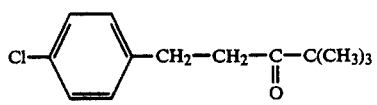

(II)

in a methanol/toluene mixture with preheated toluene and simultaneously distilling off a methanol/toluene mixture at a temperature between 65° and 110° C. until a suspension having a solids content between 10 and 70% by weight is formed, and
(b) reacting the suspension of trimethylsulphonium bromide in toluene thus obtained with 1-(4-chlorophenyl)-4,4-dimethylpentan-3-one of the formula Cl—⟨phenyl⟩—CH₂—CH₂—C(=O)—C(CH₃)₃  (III)

in the presence of solid potassium hydroxide, diethylene glycol and water at a temperature between 20° and 120° C., the amounts of the reaction components being such that per mole of 1-(4-chlorophenyl)-4,4-dimethylpentan-3-one of the formula (III) there are present
between 1 and 2 moles of trimethylsulphonium bromide of the formula (II),
between 2 and 3 moles of solid potassium hydroxide
and also
between 0.1 and 10% by weight of diethylene glycol and between 0.5 and 12% by weight of water, relative to 1-(4-chlorophenyl)-4,4-dimethylpentan-3-one of the formula (III).

2. A process according claim 1, wherein in step (a) the methanol/toluene mixture is distilled off at a temperature between 80° C. and 90° C.

3. A process according to claim 1, wherein in step (b) the temperature is between 60° C. and 90° C.

4. A process according to claim 1, wherein in step (b) 1 to 4% by weight of diethylene glycol are present relative to 1-(4-chlorophenyl)-4,4-dimethylpentan-3-one of the formula (III).

5. A process according to claim 1, wherein in step (b) 2 to 8% by weight of water are present relative to 1-(4-chlorophenyl)-4,4-dimethylpentan-3-one of the formula (III).

6. A process according to claim 1, wherein in step (a) the methanol/toluene mixture is distilled off until a suspension having a solids content between 40 and 50% by weight is obtained.

7. A process according to claim 2, wherein in step (a) the methanol/toluene mixture is distilled off until a suspension having a solids content between 40 and 50% by weight is obtained, and in step (b) the temperature is between 60° C. and 90° C., and 1 to 4% of diethylene glycol and 2 to 8% by weight of water are present relative to 1-(4-chlorophenyl)-4,4-dimethylpentan-3-one of the formula (III).

* * * * *